United States Patent [19]
Battifora et al.

[11] Patent Number: 5,002,377
[45] Date of Patent: Mar. 26, 1991

[54] MULTI-SPECIMEN SLIDES FOR IMMUNOHISTOLOGIC PROCEDURES

[75] Inventors: Hector A. Battifora, Arcadia; Parula Mehta, Glendora, both of Calif.

[73] Assignee: City of Hope, Duarte, Calif.

[21] Appl. No.: 216,676

[22] Filed: Jul. 7, 1988

[51] Int. Cl.⁵ .................. G01N 21/01; G01N 1/00; G02B 21/34
[52] U.S. Cl. .................... 350/535; 350/534; 350/536; 436/174
[58] Field of Search .............. 350/534, 535, 536; 382/6; 436/174

[56] References Cited

U.S. PATENT DOCUMENTS

| | | | |
|---|---|---|---|
| 3,736,042 | 5/1973 | Markovits et al. | 350/536 |
| 3,832,135 | 8/1974 | Drozdowski et al. | 382/6 |
| 4,647,543 | 3/1987 | Stöcker | 436/174 |
| 4,856,073 | 8/1989 | Farber et al. | 382/6 |

Primary Examiner—Bruce Y. Arnold
Assistant Examiner—James Phan
Attorney, Agent, or Firm—Edward S. Irons

[57] ABSTRACT

A process for producing a slide bearing a spaced array of specimen fragments which comprises (i) cutting at least one specimen into a plurality of narrow strips; (ii) separating the plurality into groups of specimen strips; (iii) separately positioning strips from the groups in parallel grooves in a mold; (iv) embedding the strips in the mold in a first embedding medium to provide a structure comprising a base member having opposed first and second surfaces, the first surface being substantially planar; the second surface having ridges containing a specimen strip extending therefrom; (v) forming a stack of elements, each element corresponding to the structure, with the terminal surface of the ridges of an upper structure abutting the substantially planar first surface of the next lower structure; the spaces between the ridges defining channels for receipt of a fluid; (vi) embedding the stack in a second embedding medium to form a block having a spaced array of parallel specimen strips embedded therein; the strips being so arranged that a section of the block includes a spaced array of cross-sections of each of the embedded specimen strips; (vii) dividing the block into sections each containing a spaced array of cross-sections of each of the embedded specimen strips; (viii) mounting at least one of such block sections on a slide.

18 Claims, 4 Drawing Sheets

MULTI-SPECIMEN SLIDES FOR IMMUNOHISTOLOGIC PROCEDURES

BACKGROUND OF THE INVENTION

This invention relates to multi-specimen slides useful in immunohistologic procedures. More particularly, the invention relates to slides bearing a plurality of specimens in spaced array appropriate for automated image analysis and to technology germane to such slides.

Various multi-specimen slides are known. Paraffin block sections each containing multiple tissue specimens are described in Lillie, *Histopathologic Technic and Practical Histochemistry*, McGraw-Hill, Inc., New York, N.Y. (1965) pp. 74–77. Composite snap-frozen tissue sections mounted on a slide for use in diagnostic autoimmunology are described in Nairn, *Fluorescent Protein Tracing*, 4th Ed., Churchill Livingstone, London (1976) pp. 131–138. Johnson, et al. *Handbook of Experimental Immunology*, 3rd Ed., Blackwell Scientific Publications, Oxford, England (1978) refers to composite frozen tissues useful for autoantibody testing with the admonition that "To get satisfactory sections the tissue pieces must be frozen together without leaving spaces between them . . . " (p. 154). Mason, et al. in Bullock, et al. *Techniques in Immunocytochemistry*, Vol. 2, Academic Press, London (1983) pp. 175–216 states that tissue culture supernatants may be tested against either paraffin embedded sections or cryostat sections of snap-frozen tissue. Cryostat sections may be placed in the wells of multitest slides (pp. 192–193). Mason also states that hybridoma supernatants may be tested on air dried cell smears (p. 192). Battifora describes a multitissue tumor block useful for immunohistochemical antibody testing in *Laboratory Investigation* 55:244–248 (1986). Various multitissue slides are described in Stocker U.S. Pat. No. 4,647,543.

Computer controlled automatic image analysis instruments useful with appropriate software to analyze the spaced specimen array of slides of this invention are commercially available. Typical instruments include Recognition Concepts, Inc, Gould DeAnza, Inc. and Megabesion, Inc.

SUMMARY OF THE INVENTION

This invention provides slides bearing a plurality of specimen fragments in spaced array appropriate for automated computer-controlled image analysis. The specimen fragments may be of any kind. Fixed or frozen unfixed tissue specimens and cell culture specimens are preferred. The invention also subsumes technology germane to the production and use of such slides.

DETAILED DESCRIPTION OF THE INVENTION

Slides pursuant to the invention bear a plurality of specimen fragments in a spaced array. The pattern of the array may be selected to accommodate computer controlled image analysis. Quadrangular, i.e., square or rectangular patterns are preferred.

The invention is particularly concerned with slides useful in immunohistologic procedures. Such slides typically have tissues or cell culture specimen fragments mounted thereon. Either fixed or unfixed, frozen tissue specimens may be used. For many purposes, frozen tissue slides are preferred to insure the preservation of substantially unmodified tissue components such as antigens. The tissue specimens may be stained in known manner.

Figure 1:
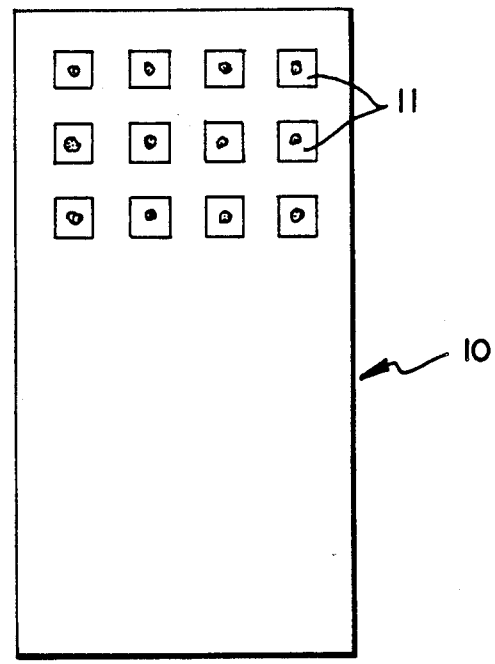
FIG. 1 is a schematic representation of a slide in accordance with the invention.

FIG. 1 illustrates a slide 10 bearing a plurality of tissue specimen fragments 11 in a substantially equally spaced rectangular array. In practice, the spacing may be arranged to accommodate automated image analysis. For example, a minimum of 3 pixels or about 75 to 100 microns space between specimens at a magnification of 25 times with a 512×512 array is appropriate.

Figure 2:
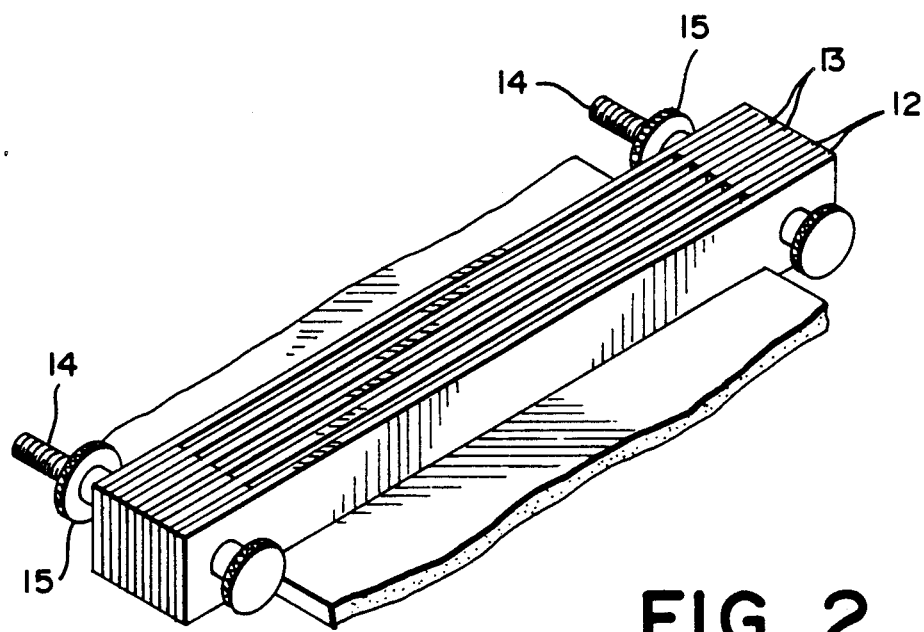
FIG. 2 is a perspective view of a multiblade device for cutting specimens into strips.

Slides in accordance with the invention are appropriately provided with fragments from a plurality of different relatively large tissue or cell culture specimens. Each relatively large specimen is cut into narrow strips in any appropriate manner, for example, with a multiblade cutting device as illustrated by FIG. 2. Referring to the figure, the device comprises a series of blades 12 separated by spacer means 13 of an appropriate dimension to provide specimen strips of a desired narrow width. The cutting device knives and spacers are mounted on support means 14, each of which includes a removable retention means 15.

The relatively large tissue specimens for subdivision into narrow strips may be obtained from any available source such as autopsies or operations. Cell culture samples may, for example, be suspended in a gel, and the gel poured over a plate and dried to provide a layer of appropriate thickness, preferably about 0.5 to about 1.5 mm, and the layer thereafter removed from the plate and cut into narrow strips with a device as shown in FIG. 2. Cell culture smears formed in known manner, see Mason, supra at page 193, comprise another source of specimen strips.

Figure 3:
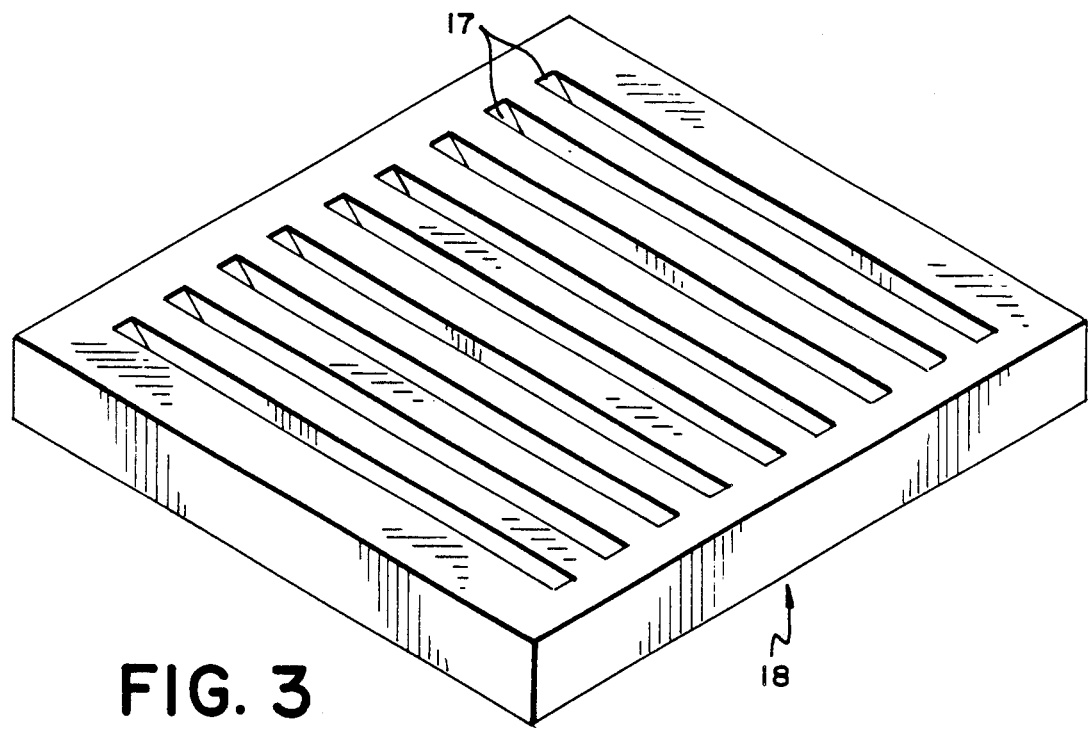
FIG. 3 is a perspective view of a mold provided with parallel grooves to receive specimen strips.
Figure 4:
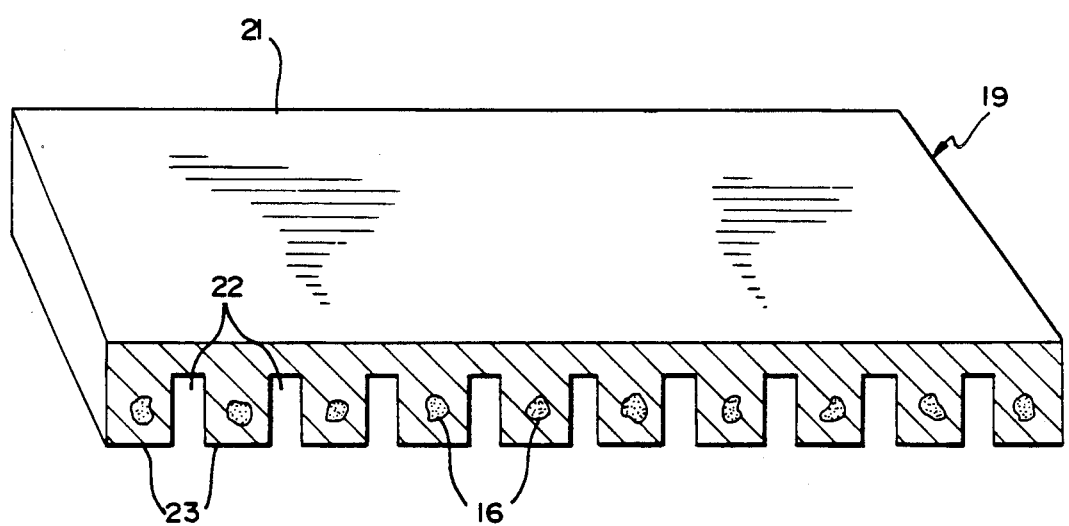
FIG. 4 is a perspective view of an embedding medium structure having specimen strips containing ridges of a type formed from the mold of FIG. 3.

Strips 16 of fixed or of unfixed frozen tissue or of cell culture are placed in the parallel grooves 17 of a mold such as the mold 18 illustrated by FIG. 3. An appropriate embedding medium, e.g., agar gel, is added to the mold containing the specimen strips and allowed to solidify thus producing a solidified embedding medium structure 19 as illustrated by FIG. 4 upon removal from the mold 18.

The structure 19 comprises embedding medium in the form of a base member 20 having a substantially planar surface 21 and an opposed surface 22 having a plurality of spaced ridges 23 extending therefrom. Each ridge 23 includes a specimen strip 16.

Figure 5:
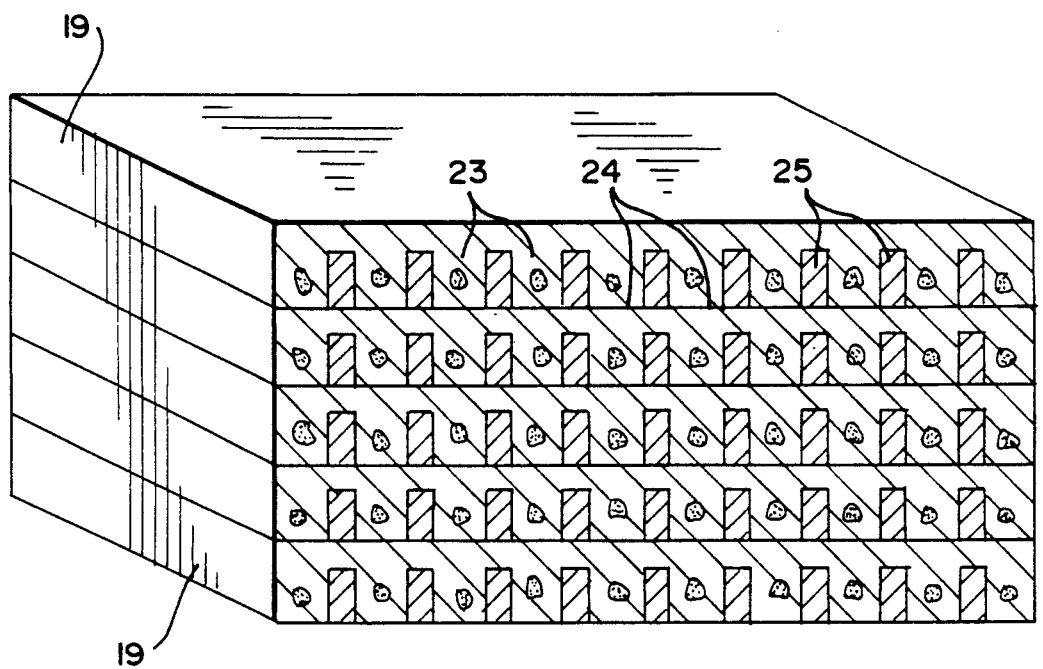
FIG. 5 is a perspective view of a stack of structures as shown in FIG. 4.

A plurality of structures 19 are stacked as shown by FIG. 5. In the stack, the terminal surfaces 24 of each ridge 23 abut the planar surface of the adjacent lower structure. The spaces between ridges provide channels 25 for access of fluids such as fixatives to the specimen strips in the ridges.

Figure 6:
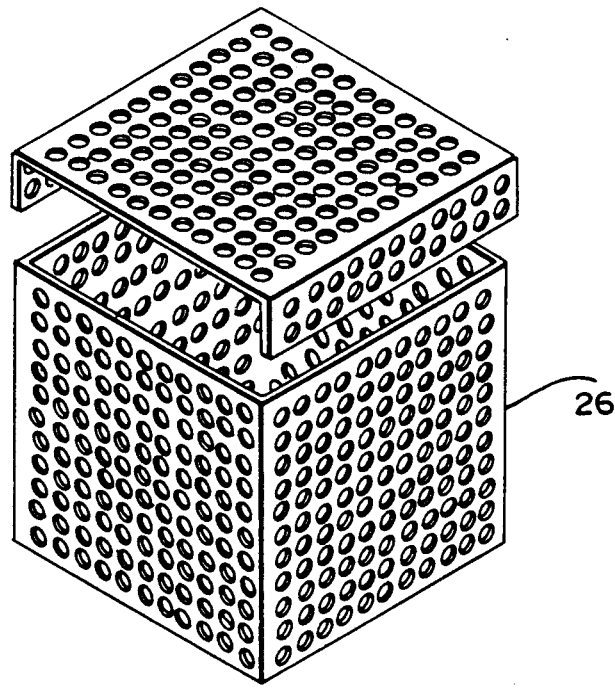
FIG. 6 is a perspective view of a container having perforated walls for receiving a stack of structures as depicted by FIG. 5.

The stack of structures is placed in a container 26 as shown by FIG. 6. The container walls include perforations 27 to permit the ingress and egress of fluids such as clearing and dehydrating agents.

A fixative may be introduced into and passed through the channels 25 to condition the specimen strips for further processing.

After fixing, the stack of structures 19 is removed from the container 26 and placed in a deep mold for final embedding to form a multispecimen block. The final embedding medium may be conventional, for example, paraffin or another wax, a high molecular weight polyethylene glycol or polyvinyl alcohol, nitrocellulose, a methacrylate resin, or an epoxy resin.

Figure 7:
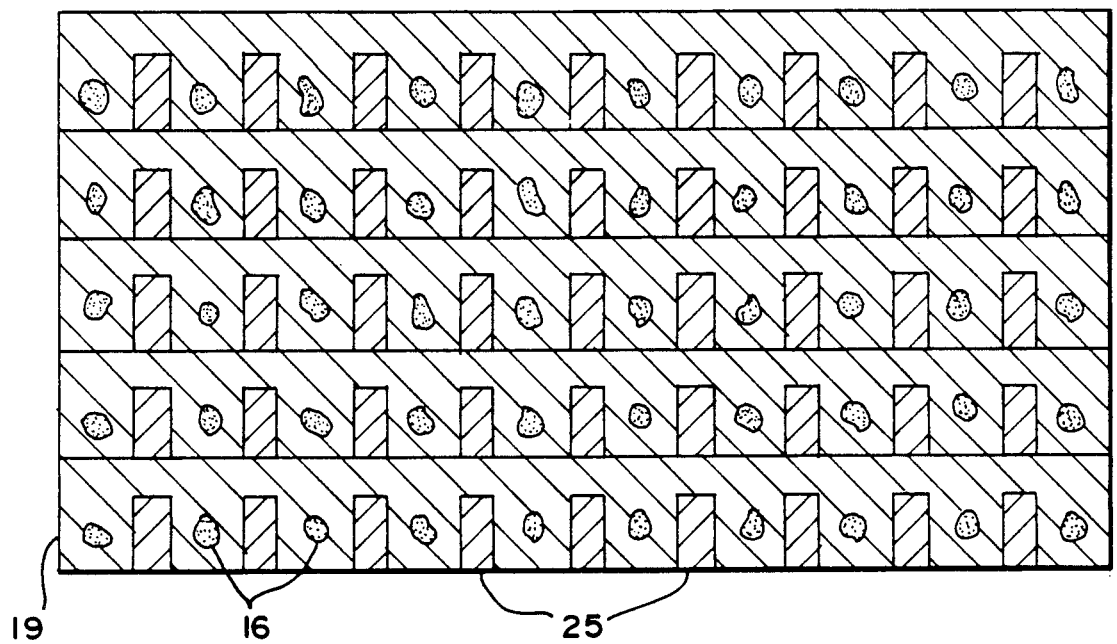
FIG. 7 is a perspective view of a section as produced by a microtome or the like of a block as depicted in FIG. 6.

The block is sectioned by a microtome or like device to provide a plurality of sections 28, each containing a spaced array of specimen sections as shown in FIG. 7. In the spaced array the channels 25 are filled by the final embedding material.

The block sections are mounted in known manner to provide slides of the kind indicated generally by the slide 10 of FIG. 1.

To produce slides of the invention bearing fragments of unfixed frozen tissue or of frozen cell cultures, snap-frozen unfixed, preferably different, specimens are cut into narrow strips, placed while frozen in the parallel grooves 18 of a mold such as the mold 18, and embedded in an embedding medium such as OCT appropriate for use in freeze drying procedures to produce frozen structures 19 of the kind illustrated by FIG. 4. Such structures, while frozen are stacked and the stack is embedded in a final embedding medium to provide a frozen block containing a plurality of spaced, parallel specimen strips as shown generally by FIG. 7. The block is sectioned, e.g., by a cryostat to provide sections containing a plurality of specimen fragments in spaced array also as shown by FIG. 7. The sections are mounted, in known manner, while frozen on slides and may thereafter be freeze dried.

Specimen fragments on the slides of this invention may be arranged in defined segments in which related specimen fragments are grouped together or associated in a manner to facilitate automated image processing. For example, one run of specimens, each of different, but known characteristics, may be positioned across a slide, e.g., a top run, to provide standards. Columns of unknown specimens may be provided above or below each standard included.

We claim:

1. A process for producing a slide bearing a spaced array of specimen fragments which comprises:
   (i) cutting at least one specimen into a plurality of narrow strips;
   (ii) separating said plurality into groups of specimen strips;
   (iii) separately positioning strips from said groups in parallel grooves in a mold;
   (iv) embedding said strips in said mold in a first embedding medium to provide a structure comprising a base member having opposed first and second surfaces,
      said first surface being substantially planar;
      said second surface having ridges containing a specimen strip extending therefrom;
   (v) forming a stack of elements, each element corresponding to said structure, with the terminal surface of said ridges of an upper structure abutting the substantially planar first surface of the next lower structure;
      the spaces between said ridges defining channels for receipt of a fluid;
   (vi) embedding said stack in a second embedding medium to form a block having a spaced array of parallel specimen strips embedded therein;
      said strips being so arranged that a section of said block includes a spaced array of cross-sections of each of said embedded specimen strips;
   (vii) dividing said block into sections each containing a spaced array of cross-sections of each of said embedded specimen strips;
   (viii) mounting at least one of such block sections on a slide.

2. A slide produced by the method of claim 1.

3. The process of claim 1 in which the specimen comprises a fixed tissue, a frozen unfixed tissue, or a cell culture.

4. The process of claim 1 in which
   (i) the specimen is a tissue fixed for storage;
   (ii) said first embedding medium is agar gel or gelatin;
   (iii) the stack of structures formed in step (v) is placed in contact with a fixative which occupies the channels defined by the spaces between the ridges of said structures;
   (iv) said second embedding medium is paraffin, polyethylene glycol, a methacrylate resin or an epoxy resin.

5. A slide produced by the method of claim 4.

6. A process for producing a slide bearing a spaced array of unfixed frozen or freeze dried tissue specimens which comprises
   (i) cutting unfixed, frozen tissue specimens into a plurality of narrow strips;
   (ii) separating said plurality into groups of frozen strips;
   (iii) separately positioning the strips from each of said groups in parallel grooves in a mold;
   (iv) embedding said so positioned strips in said mold in a cryogenic embedding medium to provide a frozen structure comprising a base member having opposed first and second surfaces
      said first surface being substantially planar;
      said second surface having a plurality of ridges containing a specimen strip extending therefrom;
   (v) forming a stack of said frozen structures with the terminal surface of said ridges of an upper stack abutting the planar surface of the next lower structure;
   (vi) embedding the frozen stack in a cryogenic embedding medium to produce a frozen embedding medium block having a spaced array of parallel specimen strips embedded therein
      said strips being so arranged that a section of said block includes a spaced array of cross-sections of each of said specimen strips;
   (vii) dividing said frozen block into sections each containing a spaced array of frozen cross-sections of each of said strips;
   (viii) mounting at least one of said frozen sections on a slide.

7. A structure comprising
   a base member formed from an embedding medium;

said base member having opposed first and second surfaces
said first surface being substantially planar;
said second surface having a plurality of spaced parallel ridges extending therefrom; and
specimen strips in at least some of said ridges.

8. A structure as defined in claim 7 in which said specimen strips are strips of fixed tissue, frozen unfixed tissue or of a cell culture composition.

9. A structure as defined by claim 7 in which said specimen strips are strips of fixed tissue and the embedding medium is agar gel or gelatin.

10. A structure as defined by claim 7 in which said specimen strips are strips of frozen, unfixed tissue and the embedding medium is cryogenic.

11. A structure as defined by claim 7 or claim 8 in which said ridges have substantially planar terminal surfaces.

12. A stack of structures as defined by claim 7 or claim 8 in which
the terminal surfaces of the ridges or an upper structure in said stack abut the substantially planar first surface of the next lower stack;
the spaces between said ridges defining parallel channels.

13. A process for substantially simultaneously fixing a plurality of tissue specimens which comprises introducing a fixative into the channels in a stack of structures as defined by claim 12 to contact the tissue specimens present in the ridges of the structures comprising said stack.

14. An embedding medium block having a spaced array of specimen strips embedded therein, said strips being so arranged that a section of said block normal to the longitudinal axis of said strips includes a spaced array of cross-sections of each of said embedded strips.

15. A block as defined by claim 14 in which specimen strips comprise fixed tissue, unfixed frozen tissue or a cell culture composition.

16. A block as defined in claim 14 in which the specimen strips comprise a cell culture composition.

17. multispecimen slide comprising a row of different specimens of known charateristics and a plurality of unknown specimens positioned above or below at least one of the known specimens in said row to provide at least a column including one known specimen and a plurality of unknown specimens.

18. A multispecimen slide as dfined in claim 17 in which said known and unknown specimens are specimens of a cell culture composition of a fixed tissue.

* * * * *

UNITED STATES PATENT AND TRADEMARK OFFICE
CERTIFICATE OF CORRECTION

PATENT NO.   : 5,002,377
DATED        : March 26, 1991
INVENTOR(S)  : Hector A. Battifora and Parula Mehta It is certified that error appears in the above-identified patent and that said Letters Patent is hereby corrected as shown below:

Column 1, line 5, after the title insert:

--This invention was made with government support under Grant No. R01 37194 awarded by the National Institutes of Health. The government has certain rights in the invention.--

Signed and Sealed this

Sixteenth Day of February, 1993

Attest:

STEPHEN G. KUNIN

Attesting Officer        Acting Commissioner of Patents and Trademarks